United States Patent [19]
Kayal et al.

[11] Patent Number: 5,766,936
[45] Date of Patent: Jun. 16, 1998

[54] REUSABLE VENTED FLASK CAP COVER

[75] Inventors: John J. Kayal, Wayne; Susan L. Barker, Tenafly; John M. Janson, Piscataway, all of N.J.

[73] Assignee: Becton Dickinson and Company, Franklin Lakes, N.J.

[21] Appl. No.: 525,893

[22] Filed: Sep. 8, 1995

[51] Int. Cl.[6] ............................................. C12M 3/00
[52] U.S. Cl. ............................ 435/297.1; 435/304.1;
435/304.3; 215/354; 215/355; 215/356;
215/357; 220/DIG. 19
[58] Field of Search ........................... 435/288.1, 297.1,
435/304.1, 304.3; 215/334, 355, 354, 356,
357; 220/DIG. 19

[56] References Cited

U.S. PATENT DOCUMENTS

| | | | |
|---|---|---|---|
| 3,326,401 | 6/1967 | DeLong | 215/261 |
| 3,870,602 | 3/1975 | Froman et al. | 435/296 |
| 4,142,940 | 3/1979 | Modolell et al. | 215/261 |
| 4,289,248 | 9/1981 | Lynn | 215/330 |
| 4,377,247 | 3/1983 | Hazard et al. | 222/517 |
| 4,387,822 | 6/1983 | Lynn | 215/330 |
| 4,765,499 | 8/1988 | Von Reis et al. | 215/261 |
| 4,770,308 | 9/1988 | Lynn | 215/330 |
| 4,935,371 | 6/1990 | Rickloff | 435/296 |
| 4,968,623 | 11/1990 | Franks | 435/285 |
| 5,010,013 | 4/1991 | Serkes et al. | 435/296 |
| 5,047,347 | 9/1991 | Cline | 435/296 |
| 5,391,496 | 2/1995 | Kayal et al. | 435/286 |

FOREIGN PATENT DOCUMENTS

| | | | |
|---|---|---|---|
| 0 040 797 | 12/1981 | European Pat. Off. | 215/226 |
| 1 295 468 | 5/1969 | Germany | 215/261 |
| 2 028 082 | 8/1978 | United Kingdom | A01G 1/04 |

*Primary Examiner*—David A. Redding
*Attorney, Agent, or Firm*—Bruce S. Weintraub; Nanette S. Thomas

[57] ABSTRACT

A vessel and closure assembly for culturing cells wherein a gas permeable membrane is provided in the closure to allow rapid and uniform equilibration of gases between the atmosphere of the vessel and the atmosphere of the incubator. A plug is provided for occluding passage of gases through the gas permeable membrane when the vessel is removed from the controlled atmosphere of the incubator.

9 Claims, 6 Drawing Sheets

REUSABLE VENTED FLASK CAP COVER

BACKGROUND OF THE INVENTION

1. Field of the Invention

This invention relates to a device for cell culture production, and more particularly to a vessel and closure assembly having means for varying the gas diffusion rate into and out of the vessel.

2. Description of Related Art

Typically, cells are cultured under conditions in which the hydrogen ion concentration (pH, the negative logarithm of the hydrogen ion concentration), temperature, humidity, osmolarity and concentration of certain ions are controlled within relatively narrow limits.

Vessels that are used in such tissue culture systems are typically made from plastic and include closures. Such vessels and closures are illustrated in U.S. Pat. Nos. 4,289,248, 4,387,822, 4,770,308 and 5,047,347.

In typical eukaryotic cell culture systems, pH is maintained near physiologic levels by utilizing a buffering system in the tissue culture fluid, in conjunction with an incubator in which carbon dioxide ($CO_2$) is infused at a rate sufficient to maintain a concentration in the incubator atmosphere of approximately 5 to 7 volume percent. The $CO_2$ reacts with water to form a weak acid and a carbonic acid, which in turn interacts with the buffering system to maintain the pH near physiologic levels. Entry of $CO_2$ from the incubator into the tissue culture vessel is generally achieved by utilizing a closure on the vessel such as, a loosely fitting cap, lid, a stopper or a cap with a mircroporous or gas permeable membrane. Equilibrium in the vessel is maintained by allowing gas exchange with the inside of the vessel and the atmosphere of the incubator while preserving sterility and preventing liquid leakage. Alternatively, a loosely fitting cap, lid or stopper is partially opened to either to an approximate extent determined by the user or by the closure design.

Removal of the vessel from the controlled atmosphere of the incubator is often required during growth and culturing of cells. The vessels are usually removed for inspection and media manipulation, subculturing or treatment of the cells and culture fluids. It is important that the pH of the cell culture be maintained close to the desired physiologic level while the vessel is outside of the incubator.

A special need exists for an improved closure assembly for a culture vessel which (1) provides rapid and uniform equilibration between the vessel atmosphere and the incubator; (2) allows the culture vessel to be removed from the controlled atmosphere of the incubator for reasonably long times without subjecting the cell culture to undesirable changes in the pH of the system; and (3) is reusable.

SUMMARY OF THE INVENTION

The present invention is a vessel comprising a chamber, an opening, a closure or other means associated with the opening, means for allowing gas diffusion into and out of the vessel and means for occluding the diffusion of gases. Most preferably, the closure seals the vessel.

Preferably, the vessel is a flask, roller bottle, tube, spinner flask, plate, dish, stirred bioreactor or any vessel that requires gas exchange. Most preferably, the vessel is a flask or roller bottle.

Desirably, the closure is a cap, push cap, threaded cap, screw cap or a stopper.

Preferably, the closure comprises a top end means for allowing gas diffusion into and out of the vessel. Preferably, the means for allowing gas diffusion is gas permeable membrane.

Further associated with the closure is means for occluding the gas permeable membrane without disturbing the seal between the closure and the vessel. Preferably, the means for occluding the membrane is a plug. The plug may be removably attached to the closure to restrict or make available the membrane to the atmosphere.

Most preferably the plug is plastic and comprises means for easy accessibility to the user.

A nearly gastight seal is superimposed when the plug is used with the closure. The plug may be removed away from the top of the cap to expose the membrane to the atmosphere. During the time the vessel is in an incubator, and the specific culture procedure requires the entire membrane to be exposed to the atmosphere of the incubator, the plug may be removed from the top of the cap to expose the membrane to the atmosphere. The plug may be reapplied to cover the membrane when the vessel is removed from the controlled atmosphere of the incubator so that the vessel may be left outside the incubator for relatively long periods of time. Therefore, by covering the membrane with the plug, substantial escape of gases from the vessel is prevented and therefore undesirable changes in the pH of the culture does not result.

The removal of the plug from the closure allows for rapid and uniform equilibration between the atmosphere in the vessel and the incubator. However, when the plug is removably attached to the closure to occlude the membrane, the vessel is a closed system and entry of microbial organisms into the vessel is prevented.

Printing may be placed on the plug or the surface of the plug may be such that additional information may be hand written on the plug.

The plug does not compromise sterility or invite leakage into the vessel when removably attached to the closure. A further advantage is that gas exchange takes place exclusively through the membrane without having to crack the vessel's cap when the plug is removed from the closure.

A further advantage of using the plug is that the need for a cap without the membrane is eliminated.

A further advantage is that the plug ensures consistency of the cell culture conditions and also facilitates the production of multiple cell cultures for large scale production. Such large scale production applications often utilize transformed or partially transformed cell lines that overproduce $CO_2$ and lactic acid when grown to very high density in order to generate significant amounts of a commercial bioproduct, such as erythropoietin (EPO) or tissue-type plasminogen activator (t-PA). In such large scale production applications wherein multiple vessels are required, each vessel in the production line can have the plug removed at the same time (obviating the need to guess on the amount of vent to provide).

Other important advantages are that the plug is reusable and that is economically feasible to manufacture.

DETAILED DESCRIPTION

Figure 1:
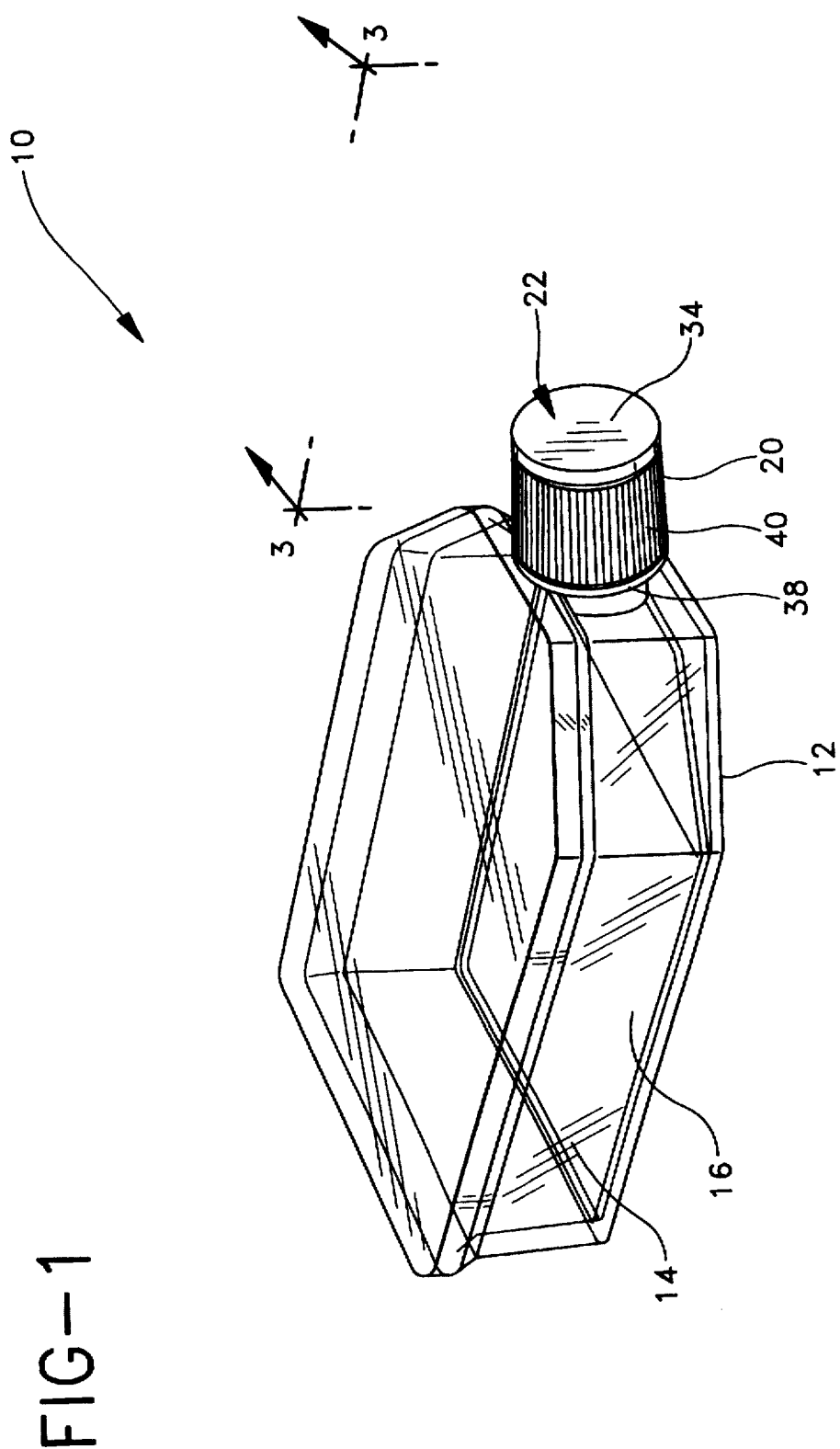
FIG. 1 is a perspective view of a flask with a cap and a plug.

While this invention is satisfied by embodiments in many different forms, there is shown in the drawings and will herein be described in detail, the preferred embodiments of the invention, with the understanding that the present disclosure is to be considered as exemplary of the principles of the invention and is not intended to limit the invention to the embodiments illustrated. Various other modifications will be apparent to and readily made by those skilled in the art without departing from the scope and spirit of the invention. The scope of the invention will be measured by the appended claims and their equivalents.

Figure 2:
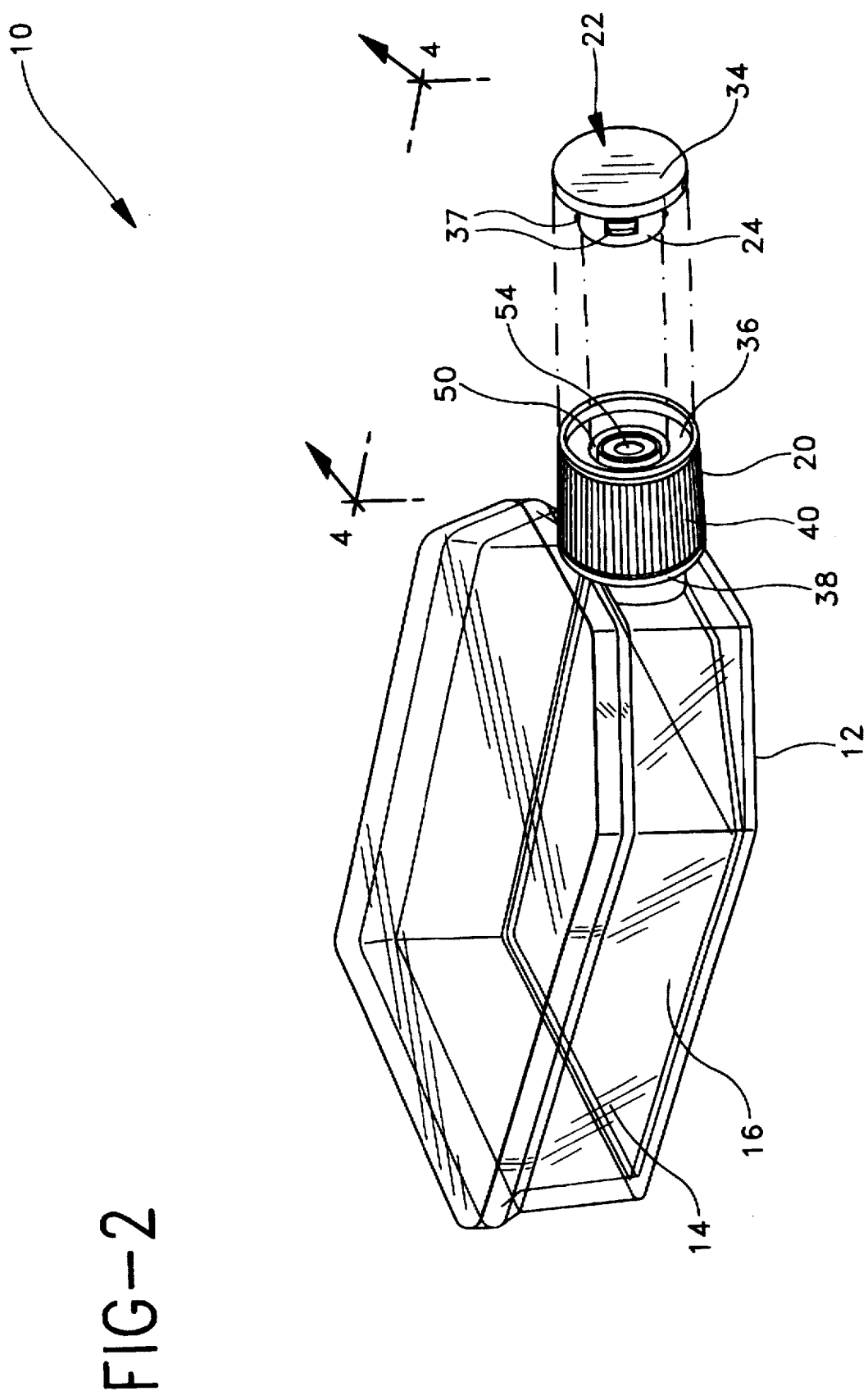
FIG. 2 is a perspective view of the flask and the cap of FIG. 1 wherein the plug is removably attached to the cap.

FIGS. 1 and 2 illustrate a cell culturing vessel 10, a flask 12, a cap 20 and a plug 22. The flask is preferably made from impact resistant plastic or glass which is gas impermeable, optically clear, non-toxic and inert with respect to the cells to be cultured.

Flask 12 has a body 14 that defines a chamber 16 in which material is adapted to be held until such time as the same is withdrawn or dispensed. It is unimportant whether body 14 is made of a collapsible or no-collapsible material, such as metals, plastics or glass.

Figure 3:
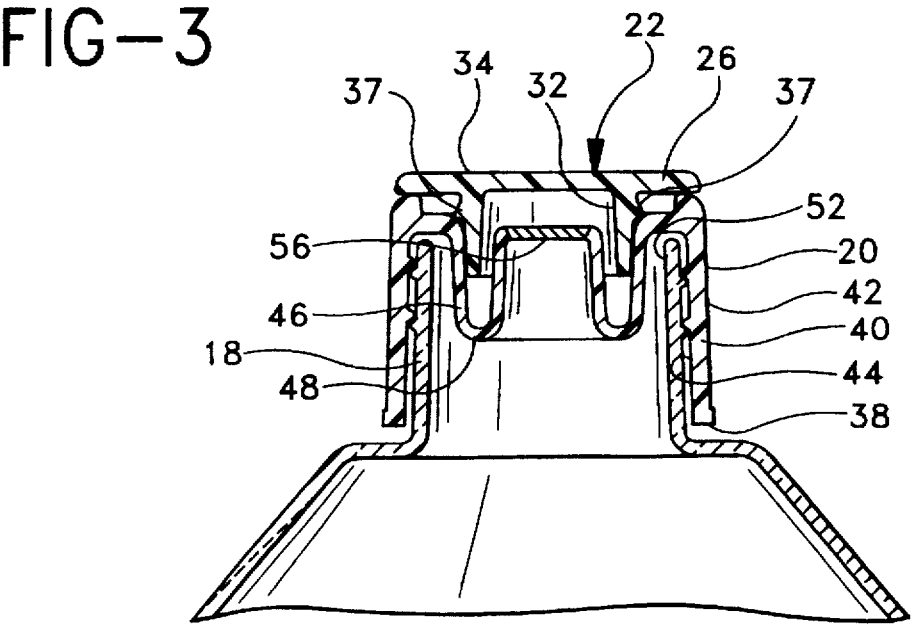
FIG. 3 is a cross sectional view of the cap and plug of FIG. 1 taken along line 3—3 thereof.
Figure 4:
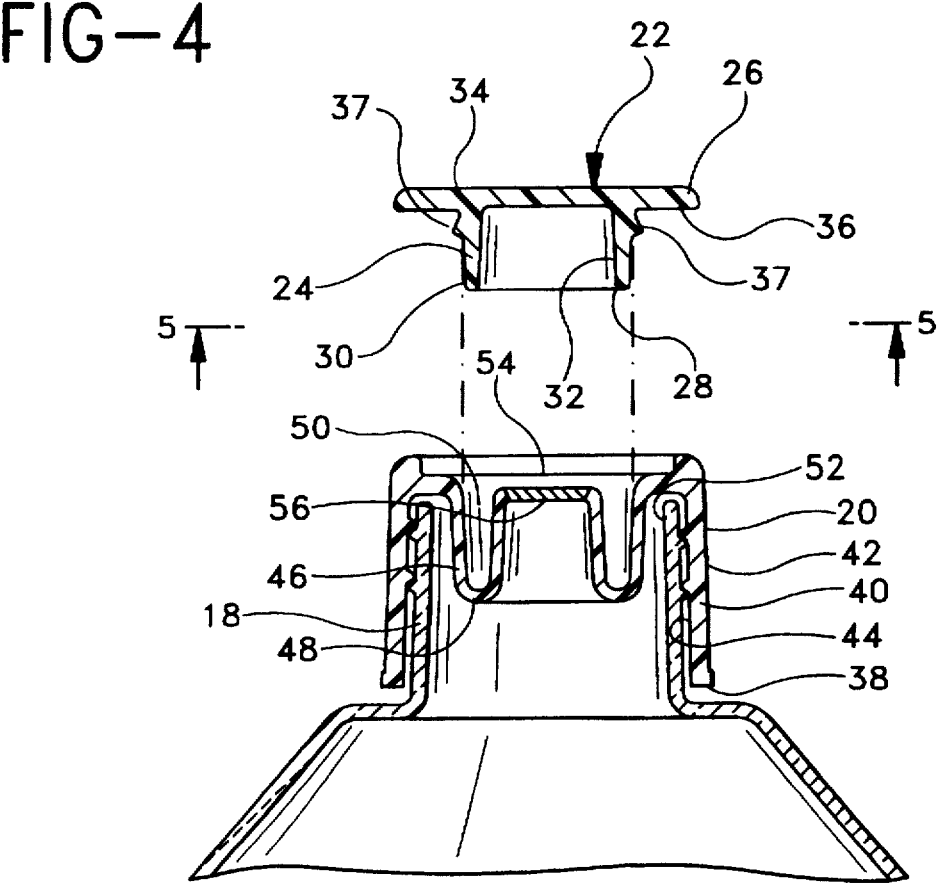
FIG. 4 is a cross sectional view of the cap and plug of FIG. 2 taken along 4—4 thereof.

As shown in FIGS. 3 and 4, flask 12 includes a neck 18 which is threaded to receive a cap 20. The neck 18 is integral with the vessel and defines a cylindrical conduit having one end integral with the vessel and the other end defining an opening through which the cells and culture fluids may be introduced into the body of the flask. Neck 18 and cap 20 constitute one of a number of well known means for introducing materials such as mammalian cells and culture fluids into body 16. As is conventionally know, cap 20 is unscrewed from neck 18 to provide an opening through which cells and culturing fluids can be introduced into the flask. The cap is subsequently screwed back onto the neck to re-seal the flask.

Figure 5:
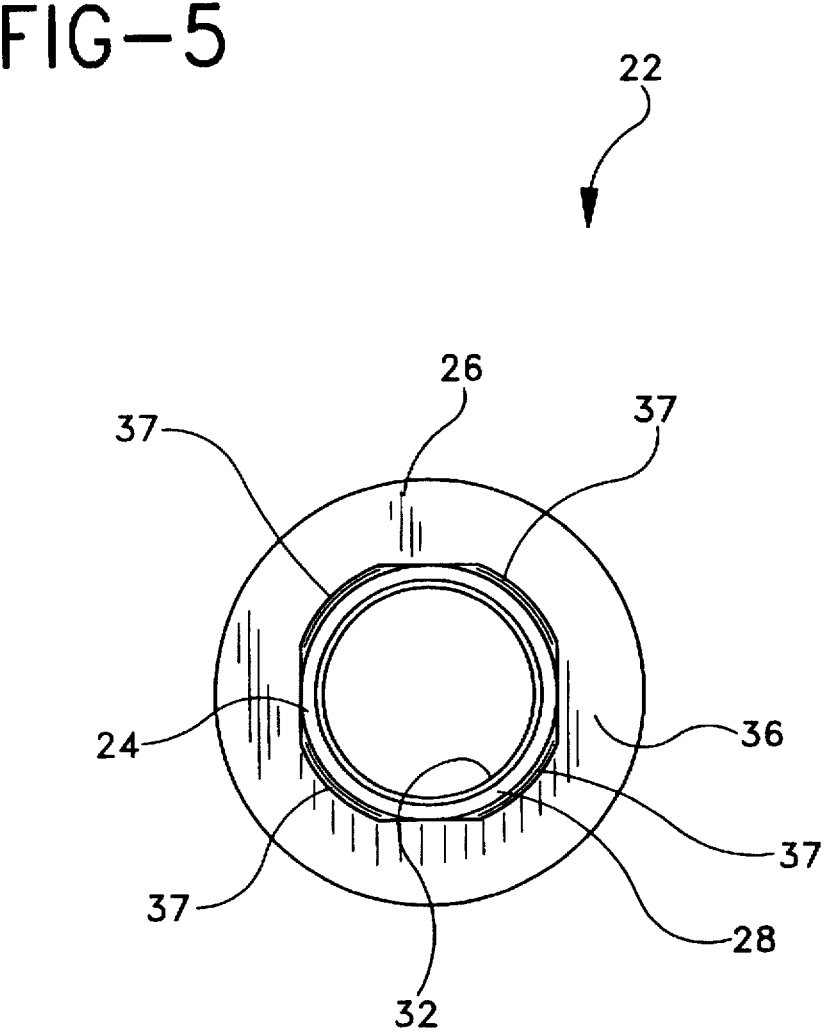
FIG. 5 is a top view of the cap of FIG. 4 taken along 5—5 thereof.

As shown in FIGS. 3, 4 and 5, cap 20 has a top surface 36, a bottom stop ledge 38, an annular outer skirt 40 extending from the top surface to the bottom stop ledge. The annular outer skirt has an outer wall surface 42 and an inner wall surface 44. Cap 20 further has an inner annular inverted recessed skirt portion 46 that extends from top surface 36 to a bottom surface 48. The inverted recessed skirt portion defines a compartment area 50 on the top surface of the cap. The inner wall surface of the annular outer skirt and the inner annular inverted recessed skirt are spaced from each other to define an annular space 52. The cap further has an orifice 54 in the inverted recessed skirt portion on the top surface. A gas permeable membrane 56 is attached to the orifice.

As shown in FIGS. 3, 4 and 5, plug 22 has a top flange 26, and a bottom stop surface 28, an annular outer skirt 24 extending from the top flange to the bottom stop surface. The annular outer skirt has an outer wall surface 30 and an inner wall surface 32. Top flange has a top surface 34 and a bottom surface 36 all of which are integrally formed. Spaced downwardly from the top flange are four lugs 37 that are located on the outer wall surface of the annular outer skirt.

The plug may be made of a molded thermoplastic material. Representative materials include, for example, polyethylene, polypropylene and polyvinyl chloride.

The gas permeable membrane 56 may be made from any suitable gas permeable material so long as it provides free passage of gases such as oxygen and carbon dioxide into body 14 while preventing bacteria and fungi from passing there through. Membrane materials provide adequate rates of carbon dioxide and oxygen permeability while preventing passage of micro-organisms. Several gas-permeable materials having suitable pore size sufficient to permit free passage of oxygen and carbon dioxide while preventing passage of bacteria and fungi are available, these materials include polyethylene, polycarbonate acrylic co-polymers and polytetrafluoroethylane.

As shown in FIG. 3, when plug 22 is removably secured to cap 20, compartment area 50 of the cap receives cylindrical base 24 of the plug. The plug is pushed into the compartment area and further inward travel of the plug is limited by the frictional contact between the base of the plug and the sides of the compartment area. When it is desired to remove the plug from the cap, the flask is held in one hand, the hanger tab is grasped with two fingers of the other hand and the flask and plug are rotated relative to one another in either direction and pulled axially out of the compartment area without difficulty. It is obvious that the plug may be reinserted into the cap and rewithdrawn therefrom innumerable times making the plug reusable for a long period of time.

In use, plug 22 is removably secured to cap 20 when the flask is outside of the controlled atmosphere of the incubator. When flask 12 is placed within the controlled atmosphere of the incubator, the plug is removed to allow communication between the gases in the incubator atmosphere and body 14 to provide rapid and uniform equilibration.

Figure 6:
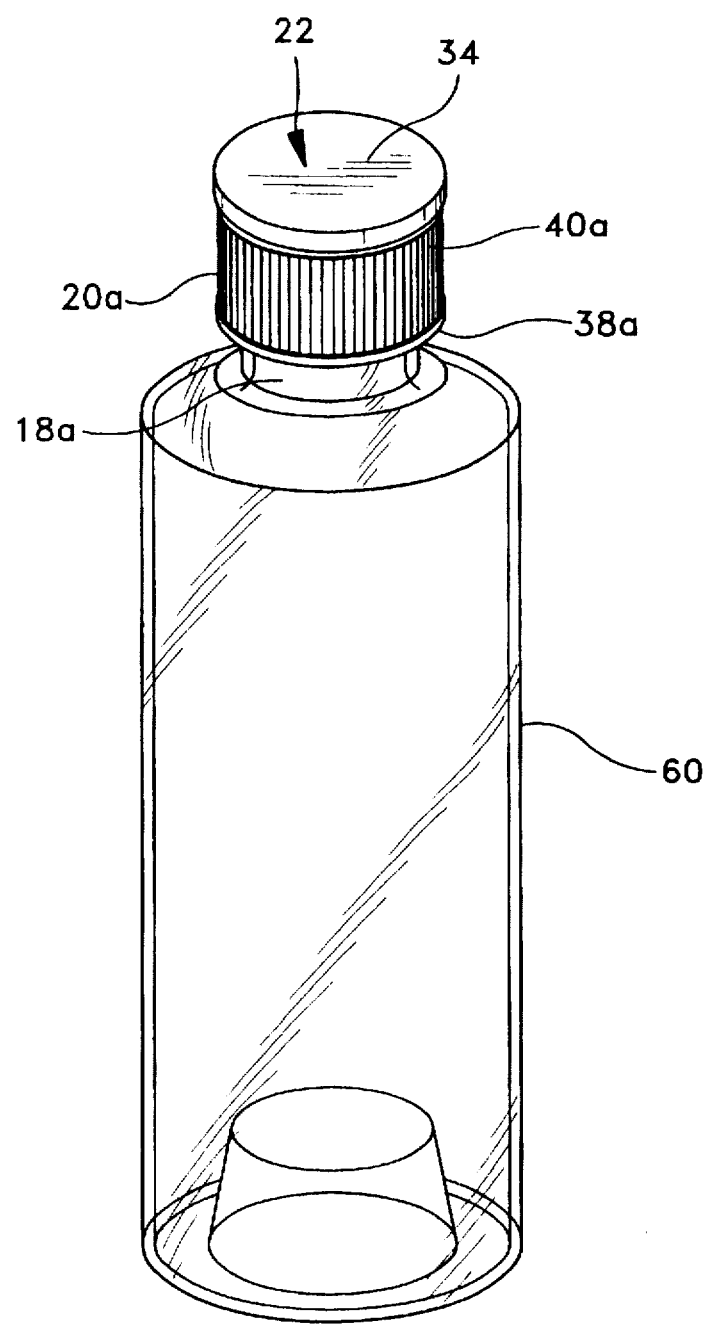
FIG. 6 is an alternate embodiment of the invention illustrating a perspective view of a roller bottle with a cap and a plug.
Figure 7:
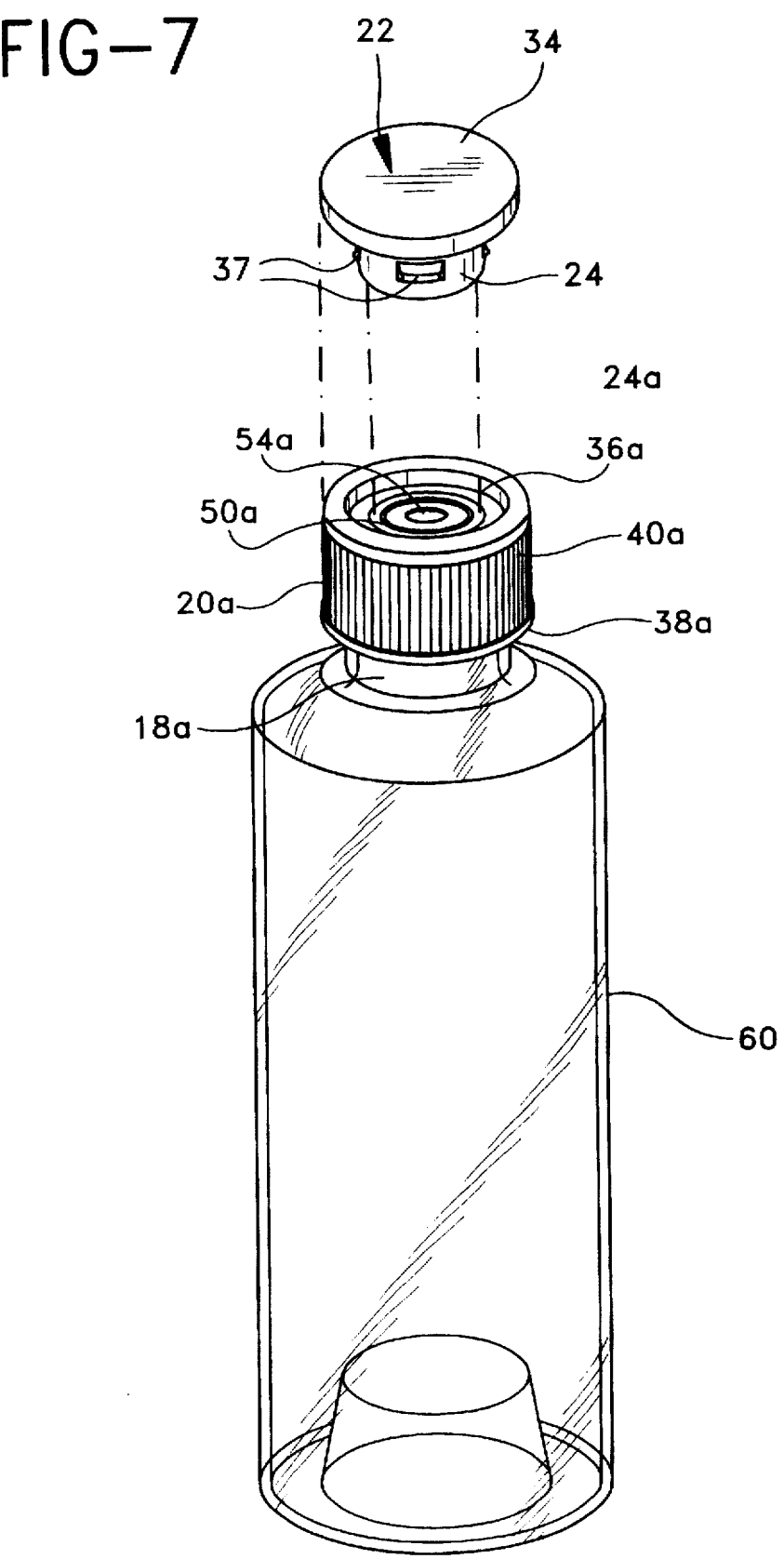
FIG. 7 is a perspective view of the roller bottle and the cap of FIG. 5 wherein the plug is removably attached to the top of the cap.

The invention, as shown in FIGS. 6 and 7 includes many components which are substantially identical to the components of FIGS. 1–4. Accordingly, similar components performing similar functions will be numbered identically to those components of FIGS. 1–5, except that a suffix "a" will be used to identify those similar components in FIGS. 6 and 7.

Roller bottle 60, cap 20a and plug 22a as shown in FIGS. 6 and 7 are an alternate embodiment of a culture vessel system that can be used inside the controlled atmosphere of the incubator to provide rapid and uniform equilibration between the gases in the incubator and the vessel.

Although the vessel in accordance with the present invention may have other uses with cell culturing systems in which gas permeability of the vessel is desired, the present invention is especially well suited for use in the constant carbon dioxide atmosphere incubators where it is desirable to allow the exchange of gases in the body of the vessel.

What is claimed is:

1. A culture vessel assembly constructed to grow cell cultures in incubators comprising:

a vessel comprising a chamber and a neck connected to said chamber having an opening for introducing cells and culture fluids into said chamber;

a cap which comprises a top portion, a bottom portion, an annular skirt extending from said top portion to said bottom portion and having an inner surface and outer surface, an inner inverted skirt portion surrounded by said inner surface of said annular skirt and extending from said top portion toward said bottom portion, an annular space between said inner surface of said annular skirt and said inverted skirt portion, a compartment area in said top portion as defined by said inverted skirt portion and an orifice in said top portion as defined by said inverted skirt portion surrounded by said compartment area, whereby said means for allowing gas diffusion into and out of said vessel is attached to said orifice; and a plug removably attached to said closure for occluding gas diffusion into and out of said vessel consisting of a top flange having a top surface and a bottom surface, a bottom stop surface, a cylindrical base extending from said top flange to said bottom stop surface and including an outer wall surface and an inner wall surface and four lugs spaced circumferentially about said outer wall surface of said cylindrical base and extending downwardly from said top flange.

2. The assembly of claim 1 wherein said means for removably mounting said closure includes a threaded portion on said neck and a mating threaded portion on said closure to provide screw type mounting of said closure to said neck.

3. The assembly of claim 1 wherein said vessel is a flask or a roller bottle.

4. The assembly of claim 3 wherein said vessel is a flask.

5. The assembly of claim 3 wherein said vessel is a roller bottle.

6. The assembly of claim 1 wherein said closure is a cap or a stopper.

7. The assembly of claim 1 wherein said means for allowing gas diffusion into and out of said vessel is a gas permeable membrane.

8. The assembly of claim 7 wherein said cylindrical base of said plug is removably secured to said compartment area of said cap whereby gas diffusion into and out of said vessel is occluded.

9. The assembly of claim 8 wherein said plug is removed from said compartment area of said cap by rotating said vessel and plug relative to one another in either direction and pulling said plug axially out of said compartment area.

* * * * *